United States Patent [19]

McCready et al.

[11] 4,254,763
[45] Mar. 10, 1981

[54] SURGICAL RETRACTOR ASSEMBLY

[75] Inventors: James F. McCready, Wollaston, Mass.; John R. Bookwalter, Putney, Vt.; Roy W. Downing, Hingham; George W. Guay, North Scituate, both of Mass.

[73] Assignee: Codman & Shurtleff, Inc., Randolph, Mass.

[21] Appl. No.: 46,534

[22] Filed: Jun. 7, 1979

[51] Int. Cl.³ .............................................. A61B 17/02
[52] U.S. Cl. ..................................................... 128/20
[58] Field of Search ............... 128/3, 20, 17, 18, 84 B; 269/328, 322

[56] References Cited

U.S. PATENT DOCUMENTS

| | | | |
|---|---|---|---|
| 2,013,892 | 9/1935 | Lucas | 128/20 |
| 2,586,488 | 2/1952 | Smith | 128/20 |
| 2,594,086 | 4/1952 | Smith | 128/20 |
| 3,394,700 | 7/1968 | Yamamoto | 128/20 |
| 3,572,326 | 3/1971 | Jensen | 128/20 |
| 3,810,462 | 5/1974 | Szpur | 128/20 |
| 4,010,741 | 3/1977 | Gauthier | 128/20 |
| 4,099,521 | 7/1978 | Nestor et al. | 128/20 |

FOREIGN PATENT DOCUMENTS

| | | | |
|---|---|---|---|
| 1235135 | 5/1960 | France | 128/20 |
| 446439 | 3/1949 | Italy | 128/20 |

Primary Examiner—John D. Yasko
Attorney, Agent, or Firm—Donal B. Tobin

[57] ABSTRACT

A surgical retractor assembly includes a support post having a lower portion and an upper portion, with the lower portion having an adjustable clamp for attaching the post to a rail provided on a surgical operating table. This clamp is capable of attachment to the rail over a flexible surgical drape. A screw mechanism is associated with the clamp so that the clamp can be attached and adjusted by the operator in an area above the rail on the surgical table. An extension rod is adjustably connected to the post and is adapted to extend in a direction generally over a patient on the operating table. A rigid ring member is connected to the extension rod for positioning a plurality of retractor blades for use on a patient. At least one retractor blade is mounted on the ring member.

12 Claims, 7 Drawing Figures

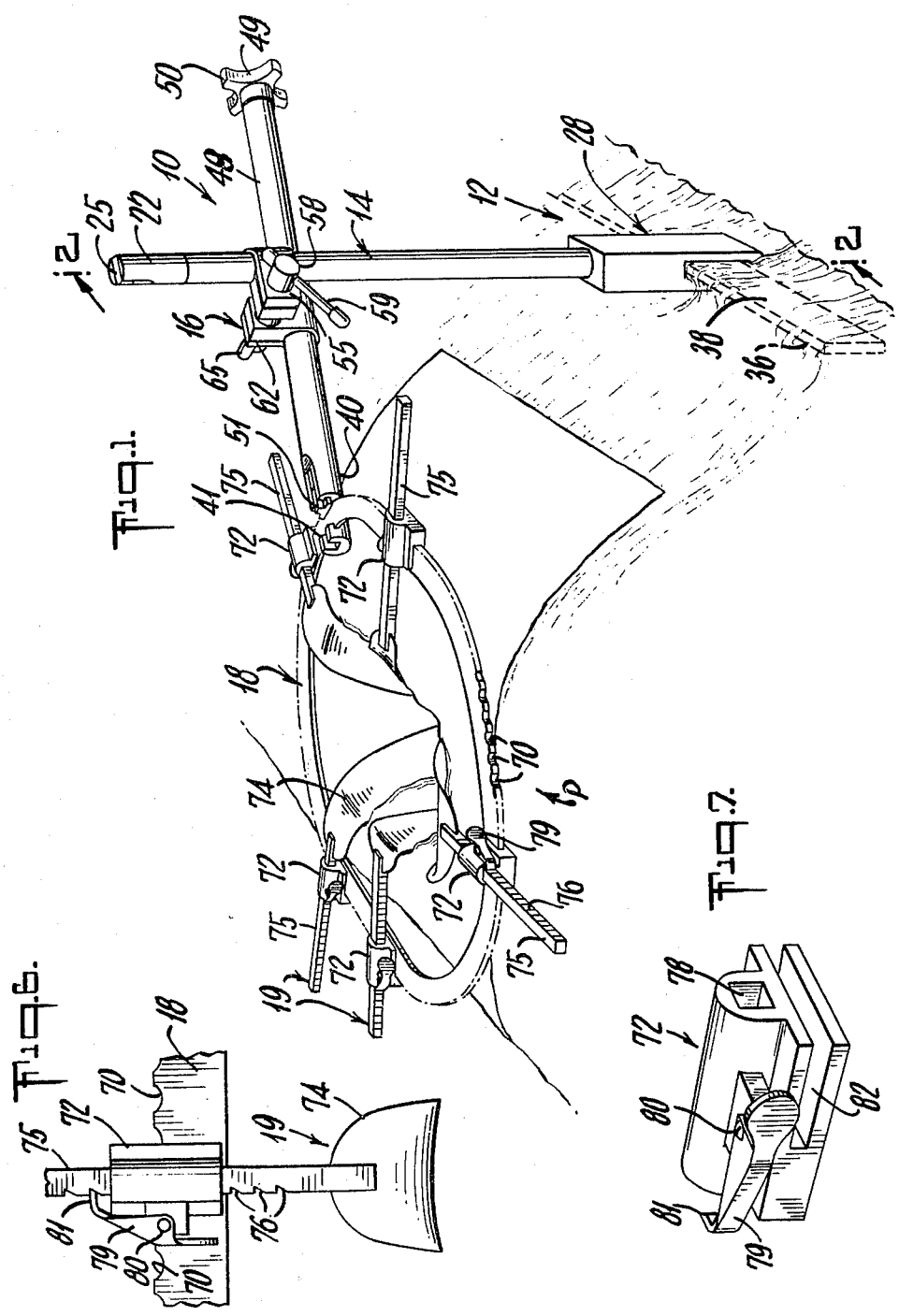

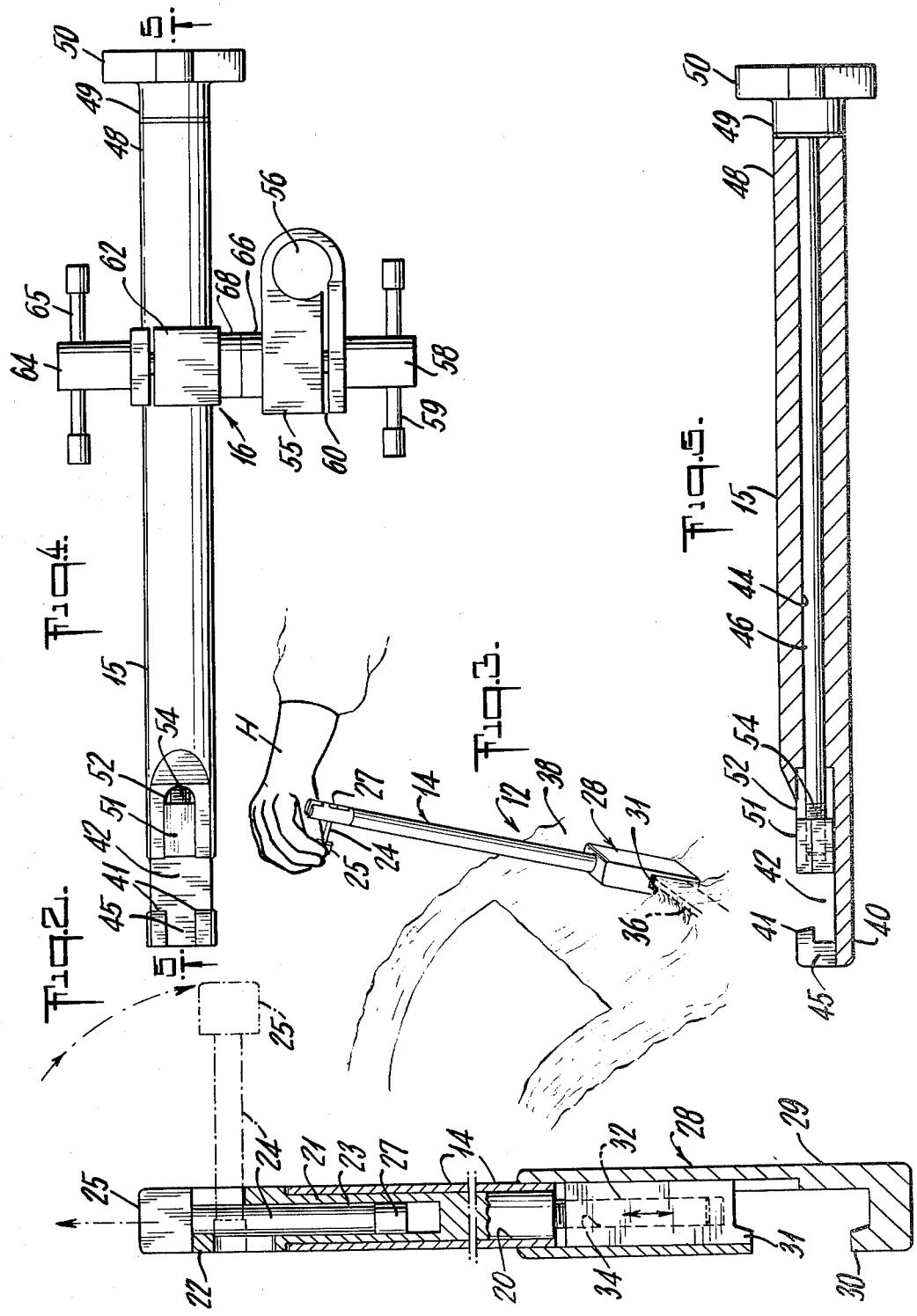

SURGICAL RETRACTOR ASSEMBLY

BACKGROUND OF THE INVENTION

The present invention relates to a surgical retractor assembly, and more particularly, concerns a surgical retractor useful in abdominal surgery and which is attached directly to the operating room table rail over either paper or linen drapes in order to maintain sterility at all times.

In surgical operations on the chest or abdomen, it is customary to employ a retraction apparatus. Most, if not all, versions of the retraction apparatus are attached directly to the operating room table by means of affixation to a rail which is provided along each side of the table. Whether by connection to one or both rails, the retraction apparatus generally provides a framework extending over the region of the patient in which the operation is to be performed. One or more retractor blades are attached to the apparatus framework, and these blades are positioned in the incision and serve to hold back tissue, organs, and the like so that the surgeon may operate on the intended area. These retractors, known as self-retaining surgical retractors, contribute to the efficiency of the surgeon, and are generally sufficiently adjustable to be useful in a variety of such surgical operations. Typical variations of this type of retractor are found in U.S. Pat. Nos. 3,572,326; 2,594,086; and 2,586,488. Although the known and available self-retaining surgical retractors offer many advantages in the operating room, some deficiencies are evident as well.

Most, if not all, of the known self-retaining retractors are attached to the operating room table rail directly, and then the surgical drape over the patient extends, as best as possible, over both the rail and the attachment portion of the surgical retractor. It is most desirable to cover the rail of the operating room table inasmuch as the rail generally establishes the line between sterile and non-sterile planes in the operating rome, i.e., above the rail is considered sterile, while below the rail is considered non-sterile. Therefore, at the attachment point where most surgical retractors are directly affixed to the rail, contamination and non-sterility are generally presumed to occur. A surgeon or sterile assistant attaching anything to the rail or elsewhere in this lower region would have to wear a double set of gloves, the outer set being discarded before proceeding with the operation. Moreover, any attempt during surgery to move the retractor by an adjustment at its attachment point on the rail would also involve the problem of invading the non-sterile lower plane of the operating room, below the line established by the attachment rail.

Merely placing the surgical drape over the rail first, and then attaching the surgical retractor to the rail over the drape will not solve this invasion of the non-sterile area if the clamp tightening mechanism is at or near the rail, as is the case with known self-retaining surgical retractors. Whereas the drape may serve to cover the non-sterile rail and some of the region below, the surgeon or assistant may still have to drop his hands near or into the non-sterile region in order to tighten the retractor clamp to the rail. This means that there may be an exposure to the non-sterile region below the rail, with the attendant risks of contamination. Accordingly, it can be appreciated that improvements are needed, particularly in the manner of attaching self-retaining surgical retractors to the operating room table while not invading the non-sterile region. It is particularly to the solution of that problem, and others as well, that the present invention is directed.

SUMMARY OF THE INVENTION

The surgical retractor assembly comprises a support post having a lower portion and an upper portion. The lower portion includes an adjustable clamp means for attaching the post to rail means provided on a surgical operating table. Means for adjusting the clamp means is positioned above the clamp means so that the clamp attachment can be performed by the operator in an area above the rail means. Extension means is adjustably connected to the post and is adapted to extend in a direction generally over a patient on the operating table. Means for positioning at least one retractor blade for use on a patient is connected to the extension means, and a retractor blade is mounted on the positioning means.

In the preferred embodiment of the present invention, the adjustable clamp means is a C-type clamp being capable of attachment to the rail means over a flexible surgical drape. This clamp is controlled and adjusted by a rotative screw mechanism extending through the support post so that the operator can turn the same at the upper end of the post for operating the adjustable clamp. The positioning means is preferably a substantially flat, oval-shaped ring member having an open center. The outer periphery of this ring member has a plurality of spaced indentations to facilitate the position at which the ring member is connected to the extension means. Preferably, a plurality of retractor blades is mounted on the ring member, with each blade being adjustable both in its annular position on the ring member and in a general radial direction toward the open center of the ring member.

From the structural standpoint, the surgical retractor assembly of the present invention is notably different from prior retractor assemblies in a number of respects. For instance, the present retractor assembly is capable of attachment to the rail on the operating table over standard surgical draping or linen. Moreover, this attachment is facilitated by adjusting the attachment clamp from the upper portion of the support post so that the hands of the surgeon or assistant will remain in the sterile region. As mentioned above, known prior retractors of the self-retaining type are attached directly to the rail on the table by a clamp or locking feature adjustable at or near the rail so that the hands of the surgeon invade, or come close to invading, the non-sterile region thereby requiring special mounting techniques to preserve sterility. In accordance with the principles of the present invention, its structure therefore provides a number of advantages over prior surgical retractors of the self-retaining type. In addition to providing an attachment feature to keep the surgeon's hands in the sterile region of the operating room, the present invention may be moved readily along the rail or re-positioned even after surgery has started. Once again, this re-positioning feature is facilitated by the location of the clamp adjusting device in or on the upper portion of the support post of the present invention. Employment of a single support post of strong material, in the preferred embodiment, provides a cantilever extension from only one side of the operating table, thereby leaving more room for the surgeon and the assistants to move about; moreover, the preferred ring member is controllable to have its height, horizontal orientation and angularity with respect to the patient adjusted to the proper position for the specific operation at hand. Also, in the preferred embodiment of this invention, the position of the ring member over the patient is adjustable by a tightening device at the proximal end of the extension rod; thus, the ring can be readjusted at any time during surgery without compromising the sterile technique. Allowing the surgeon or assistant to control this adjustment at the proximal end of the extension rod eliminates the undesirable reaching over the patient to perform this type of adjustment. A quick-release ratchet mechanism is also provided to attach the retractor blades to the ring member. As in other known self-retaining retractor devices, no wing nuts or screws are required in this invention in order to make the attachment of retractor blade to the ring member.

BRIEF DESCRIPTION OF THE DRAWINGS

FIG. 1 is a perspective view illustrating the preferred surgical retractor assembly attached to a surgical operating table and ready for use in a surgical operation on a patient.

FIG. 2 is a cross-sectional view taken along line 2—2 of FIG. 1;

FIG. 3 is a perspective view illustrating the attachment of the support post to the rail on an operating table, as the first step of assembling the retractor assembly;

FIG. 4 is a top plan view of the elongate extension rod and coupling device to attach same to the support post;

FIG. 5 is a cross-sectional view taken along line 5—5 of FIG. 4;

FIG. 6 is a top plan view of one retractor blade attached to the ring member, shown in partial view; and FIG. 7 is an enlarged perspective view of the preferred pawl mechanism for attaching the retractor blade to the ring member.

DETAILED DESCRIPTION

While this invention is satisfied by embodiments in many different forms, there is shown in the drawings and will herein be described in detail a preferred embodiment of the invention, with the understanding that the present disclosure is to be considered as exemplary of the principles of the invention and is not intended to limit the invention to the embodiment illustrated. The scope of the invention will be pointed out in the appended claims.

Adverting to the drawings, particularly to FIG. 1, there is illustrated a self-retaining surgical retractor assembly 10 attached to a surgical operating room table 12 and in a position as it would appear during an operation on a simulated patient P. The main components comprising this surgical retractor are an elongated support post 14, an elongate extension rod 15 which is connected to support post 14 by a coupling device 16, a substantially flat, oval-shaped ring member 18 adjustably affixed to extension rod 15 and a plurality of retractor blades 19 adjustably mounted on ring member 18.

Turning to FIGS. 2 and 3 in conjunction with FIG. 1, support post 14 is illustrated in greater detail with the functional purpose it serves. This support post is essentially an elongate cylindrically-shaped metal tube with the lumen 20 extending along the longitudinal axis. An elongate shaft 21 extends through lumen 20 and terminates at the upper end of the post in a knob 22 which preferably has an outside diameter the same as that of the support posts so that the same are size-compatible. Shaft 21 is loosely fit in lumen 20 so that both it and the connected knob are free to turn. To facilitate this turning ability, a longitudinal bore 23 is provided extending a short distance into the central portion of the shaft. A lever arm 24 with a collar 27 on its bottom end is slidably positioned in the longitudinal bore. Collar 27 has a slightly larger diameter than lever arm 23. A tommy bar head 25, providing a substantial T-like effect, is provided on the upper end of lever arm 23. When not using the lever arm for tightening purposes, it is stored within the bore so that it is out of the way. To use for tightening, the arm and bar are lifted vertically out of the bore, and then swung outwardly through recess 26 in knob 22, as seen in the phantom lines of FIG. 2. Collar 27 is sized to be larger than the width of recess 26 to provide entrapment of the arm in the outwardly extending position. Thus, the operator now has a ready handle for turning the knob and connected shaft, as seen in FIG. 3.

At the lower portion of support post 14 is an adjustable clamp assembly 28. This clamp assembly includes a box-shaped structure 29 which is connected to the lower end of the tubular support post 14. The lowermost end of box structure 29 is formed into a C-type lower clamp 30. Inside box structure 29 is an upper clamp 31. Upper clamp 31 is substantially U-shaped in appearance with the inside surface of this U adapted to threadably fit over the lowermost end of shaft 21. Mating internal threads 32 on the inside surface of upper clamp 31 and external threads 34 on the lower end of shaft 21 provide the engaging surfaces between upper clamp 31 and shaft 21. Accordingly, rotative movement of shaft 21 and knob 22 will cause upper clamp 31 to move in an axial direction. This axial movement of upper clamp 31 thereby provides the tightening mechanism whereby support post 14 can be attached to the surgical operating table. This attachment is more clearly seen by referring to FIG. 3.

On a standard operating room surgical table 12, a rail 36 is provided on each side generally extending the length of the table. As alluded to above, this rail is commonly accepted as being in the non-sterile region so that contact with the rail could cause contamination. To take advantage of the features of the present invention, a sterile, surgical drape or linen 38 is placed in position over a patient and is allowed to cover rail 36, thereby providing protection from this non-sterile area. Support post 14 is then attached by positioning clamp assembly 28 on to the rail, preferably over the flexible surgical drape. Note that the surgeon's hand H grasps lever arm 24 at the upper end of the support post for turning knob 22 which controls the movement of upper clamp 31 for the tightening effect. With this structural configuration, the support post is attached and the clamp adjusted and tightened by the surgeon in an area well above rail 36, which clearly keeps the surgeon's hands in the sterile region. Once the clamp has been sufficiently tightened, support post 14 extends in a substantially vertical direction, as seen in FIG. 1, and is thereby ready to receive the remaining components of this retractor assembly.

Turning now to FIGS. 4 and 5, extension rod 15 and coupling device 16 are illustrated in greater detail. Extension rod 15 is similar in many respects to support post 14, is elongate in nature and is preferably metal in order to lend strength to the composite structure. The distal end 40 of the rod is formed to provide a hook serving as a first jaw 41. A slot in distal end 40 serves to provide a gap in this distal end of the extension rod. A through bore 44 extends through the remaining portion of elongate rod 15, with this bore generally being drilled during fabricating which thereby provides the gap 45 between segments of first jaw 41. Extending through bore 44 is an elongate shaft 46 which terminates at the proximal end 48 of elongate rod in a handle 49. The base of handle 49 is substantially the same outside diameter as the elongate rod, while also including a number of flanges 50 to facilitate gripping by the operator. Both shaft 46 and connected handle 49 are free to turn with respect to elongate rod 15.

A movable second jaw 51 is positioned adjacent slot 42 and within an axial groove 52 formed in the distal end of rod 15. This second jaw is connected to the distal end of shaft 46, and by a mating threaded engagement 54 is adapted to move axially upon rotative movement of shaft 46 and handle 49. This axial movement of second jaw 51 with respect to first jaw 41 thereby allows the tightening effect for ring member 18 which fits into slot 42 for proper placement in this assembly. Of particular note, the operator of this retractor assembly can adjust ring member 18 by performing the tightening movement at the proximal end of the elongate rod rather than reaching over the patient to the distal end for tightening.

To connect elongate extension rod 15 to vertical post 14, coupling device 16 is provided. A vertical coupler 55 includes a circular opening 56 which slidably fits around the outside diameter of post 14. A tightening screw 58 and wrench arm 59, in conjunction with a narrow slot 60 in coupler 55 allow the coupler to be tightened to support post 14. This arrangement allows not only a height adjustment for the height of extension rod 15, but also rotative angularity in the direction over the patient. A horizontal coupler 62 is provided for the elongate rod 15, and is similar to vertical coupler 55. Horizontal coupler 62 allows rod 15 to be adjusted both in the translational direction of the rod and for angularity with respect to the vertical axis. Tightening screw 64 and wrench handle 65 for the horizontal coupler act independently from the corresponding components on the vertical coupler. Thus, it can be seen that the abutment sections 66 and 68 of the respective vertical and horizontal couplers can be freely rotated with respect to each other.

Referring now more particularly to FIGS. 1, 5 and 6, ring member 18 is illustrated as being substantially oval in shape with an open center area which provides a large region for the retractor blades to perform their function. The ring member is adjustably connected to the elongate rod by being positioned with the flat surface into slot 42 at the distal end of the elongate rod. First jaw 41 and second jaw 51 are then tightened around the ring member to affix it in position. To facilitate this fixed positioning, ring member 18 includes a plurality of spaced indentations 70 around its entire outer periphery. Second jaw 51 at the distal end of elongate rod 15 may be designed so that a portion of it matingly fits in an indentation 70 on the ring member to assure a tight locking effect. Thus, the ring member may be rotated in a variety of positions to assist the surgery team in placing the ring and retractor blades in the required position for the surgical procedure. The cantilever effect of both the elongate extension rod 15 and the further extension provided by rigid ring member 18 allows the entire retractor assembly to sufficiently reach across the patient so that this assembly can be located only on one side of the patient, without requiring a second support arm on the other side of the patient as is common in many prior self-retaining retractor devices.

In FIGS. 6 and 7, one retractor blade 19 is shown mounted on ring member 18 with its quick-release pawl attachment mechanism 72. The retractor blade includes the blade portion 74 which is inserted into an incision for restraining tissue, organs and the like during the surgical procedure. A handle 75 extends from blade 74 and, in the embodiment being described, preferably has a square or rectangular cross-section. Along one surface of handle 75 is a plurality of spaced ratchet teeth 76 which are spaced to provide small incremental adjustments of the handle. Handle 75 is inserted through a compatible opening 78 extending through pawl mechanism 72, as seen in FIG. 7. Teeth 76 on the handle face a spring-loaded pawl 79 which is connected by a pivot pin 80 to the pawl mechanism. The leading edge 81 of pawl 79 mates with teeth 76 and thereby locks the handle in a fixed position. Pawl mechanism 72 is slid on to ring member 18 by means of a slot 82 through the body of the pawl mechanism. Slot 82 is open to the opposite surface from that surface which leading edge 81 of the pawl extends. Although not seen in FIG. 7, slot 82 may incorporate a dowel or other pin with a smooth radius to matingly fit into an indentation 70 on ring member 18, to hold the pawl mechanism securely on to the ring member. By referring to FIG. 6, it can be seen that pawl mechanism 72 holds retractor blade 19 so that the handle extends in a general radial direction and is thus adjustable in the radial direction by means of pawl 79 and ratchet teeth 76. It is appreciated that pawl mechanism 72 requires no screws, wing nuts, or other fixation devices inasmuch as the inwardly directed radial force transmitted from blade 74 during use of the retractor tends to maintain the pawl mechanism in position on ring member 18. This type of pawl mechanism mounting with the various retractors can be seen by referring to FIG. 1, which shows retractor blades 74 in a position as they may appear during a surgical operation on a patient P. It can be seen that each retractor may be adjustably positioned to any desirable annular position on ring member 18; also, each retractor blade may be adjusted in a general radial direction toward or away from the open center of the ring member.

Thus, a self-retaining surgical retractor assembly is provided which is useful particularly in chest or abdominal cavity surgery, and which is connected to the operating room surgical table over the surgical drape with the tightening mechanism positioned at the upper portion of the support post to assure that the surgeon's or assistant's hands are maintained in the sterile region during assembly and affixation of the retractor to the table.

We claim:

1. A surgical retractor assembly adapted for attachment to the rail of a surgical table comprising:
    an elongate support post having a lower portion and an upper portion, said lower portion including adjustable clamp means for attaching the post substantially vertical to said rail;
    said upper portion of said post including clamp adjustment means operatively connected to said adjustable clamp means so that the attachment and adjustment of said clamp means can be performed by the operator in an area above said rail;
    extension means adjustably connected to said post for supporting a rigid ring means over a patient on said operating table and adapted to extend in a direction generally over a patient on said operating table;

rigid ring means connected to said extension means at only one point thereof so as to cantilever said ring means over a patient for positioning a retractor blade for use on a patient; and, at least one retractor blade mounted on said ring means.

2. The assembly of claim 1, wherein said adjustable clamp means includes a C-type clamp being capable of attachment to said rail means over a flexible surgical drape.

3. The assembly of claim 1, wherein said clamp adjusting means includes a first rotative mechanism extending from said upper portion to said lower portion of said support post associated with said clamp means, said first rotative mechanism including turning means disposed at said upper portion of said post for turning said first rotative mechanism and thereby operating said adjustable clamp means.

4. The assembly of claim 1, wherein said extension means includes an elongate rod, and further including a coupling device having a vertical coupler means for adjustably affixing said coupling device to said post; and, having a horizontal coupler means for adjustably affixing said rod to said coupling device.

5. The assembly of claim 4, wherein said elongate rod includes a distal portion and a proximal portion, said distal portion including an open adjustable jaw section means for receiving said ring means and for gripping the same tightly, said open jaw section means surrounding said ring on less than all sides.

6. The assembly of claim 5 wherein said adjustable jaw section means includes a second rotative mechanism extending from said distal portion to said proximal portion of said elongate rod, said second rotative mechanism including turning means disposed at said distal portion of said rod for turning said second rotative mechanism and thereby operating said adjustable jaw section.

7. The assembly of claim 1, wherein said retractor blade includes a handle having ratchet teeth along one side thereof, said handle being mounted to said ring means in conjunction with a pawl mechanism which is adapted to clevis over said ring means and receive said handle so that said handle extends in a general radial direction and is adjustable in said radial direction by an operable pawl on said mechanism which mates with said teeth.

8. A surgical retractor assembly adapted for attachment to the rail of a surgical table comprising:

a support post having a lower portion and an upper portion, said lower portion including adjustable clamp means for attaching the post to said rail;

said upper portion of said post including clamp adjustment means operatively connected to said clamp means so that the attachment and adjustment of said clamp means can be performed by the operator in an area above said rail;

extension means adjustably connected to said post for supporting a ring means over a patient on said operating table and adapted to extend in a direction generally over a patient on said operating table;

means connected to said extension means at only one part thereof so as to cantilever said ring means over the patient for positioning at least one retractor blade for use on a patient; and, a retractor blade mounted on said positioning means.

9. A surgical retractor assembly for attachment to a drape-covered rail provided on a surgical operating table comprising:

an elongate support post having a lower portion and an upper portion, said lower portion including an adjustable clamp for clampingly attaching the post substantially vertically to said drape-covered rail;

a rotative mechanism extending from said upper portion to said lower portion of said support post associated with said clamp said rotative mechanism including turning means disposed at said upper portion to said post for turning said rotative mechanism and thereby operating said adjustable clamp so that the attachment and adjustment of said clamp can be performed by the operator in an area above said rail;

an elongate rod extending in a direction generally over a patient on said operating table, and further including a coupling device having a vertical coupler means for adjustably affixing said coupling device to said post and having a horizontal coupler means for adjustably affixing said rod to said coupling device said rod including a distal end and a proximal end;

an open adjustable jaw section at said distal end and a control mechanism at said proximal end for operating said adjustable jaw section;

a rigid ring member having an open center adjustably affixed in the open jaw section of said rod;

a plurality of retractor blades mounted on said ring member, each blade being adjustable both about the periphery of said ring member and in a general radial direction toward the open center of said ring member.

10. The assembly of claim 4 wherein said vertical coupler and said horizontal coupler each have an abutment end disposed in confronting relationship and cooperatively adapted to rotate with respect to each other.

11. The assembly of claim 1 wherein said elongate post includes:

a hollow tube extending from said upper portion to said lower portion;

a clamp assembly attached to the lower portion of said tube and including:

a hollow box-type assembly having a top and a bottom, left and right sidewalls, and front and back walls, said top fixedly receiving said lower portion of said tube;

said front wall and said left and right sidewalls having openings therein cooperatively defining a C-type slot in said box-type assembly for receiving said rail;

the interior of said back wall including a recess;

said clamp assembly further including an upper clamp slidably positioned within said box-type assembly and engaging said recess;

said upper clamp including a threaded bore facing said hollow tube;

a shaft slidably positioned in said tube and including a threaded extension threadably inserted in said threaded bore and a knob extending out of said tube;

a lever operatively affixed to said shaft for rotating said shaft.

12. The assembly of claim 1 wherein said extension means includes:

an elongate rod having a distal portion and a proximal portion;

said distal portion including a U-shaped slot extending transversely across said rod and spaced apart from the distal end of said rod;

said distal end including at least one hook projecting into said U-shaped slot from said first sidewall thereof;

a groove extending generally axially along said rod from said second slot wall, said groove defined by left and right sidewalls;

a bore extending generally axially along said rod from said proximal end and extending into said groove;

a handle disposed at the proximal end of said rod;

a shaft fixed to said handle and slidably extending through said bore into said slot;

said shaft including threads at its distal end;

a jaw movably disposed in said slot and threadably affixed to said shaft so that as said shaft is turned, said jaw will move toward or away from said first sidewall of said U-shaped slot;

said jaw including a hook extending toward said first sidewall of said slot;

said first and second hooks cooperative providing means for holding said ring against rotation in a plane perpendicular to the plane of the ring.

* * * * *

UNITED STATES PATENT AND TRADEMARK OFFICE
CERTIFICATE OF CORRECTION

PATENT NO. : 4,254,763
DATED : March 10, 1981
INVENTOR(S) : John R. Bookwalter et al.

It is certified that error appears in the above-identified patent and that said Letters Patent are hereby corrected as shown below:

At Column 8, Line 15, "to" should be -- of --.

Signed and Sealed this

Tenth Day of November 1981

[SEAL]

Attest:

GERALD J. MOSSINGHOFF

Attesting Officer

Commissioner of Patents and Trademarks